US006582446B1

United States Patent
Marchosky

(10) Patent No.: US 6,582,446 B1
(45) Date of Patent: Jun. 24, 2003

(54) METHOD AND APPARATUS FOR PERCUTANEOUS OSTEOPLASTY

(76) Inventor: J. Alexander Marchosky, 224 S. Woods Mill Rd., Suite 610 South, Chesterfield, MO (US) 63017

( * ) Notice: Subject to any disclaimer, the term of this patent is extended or adjusted under 35 U.S.C. 154(b) by 0 days.

(21) Appl. No.: 09/560,950

(22) Filed: Apr. 28, 2000

Related U.S. Application Data

(60) Provisional application No. 60/132,852, filed on May 6, 1999.

(51) Int. Cl.⁷ ................................................ A61B 17/32
(52) U.S. Cl. ............................ 606/167; 606/92; 606/94
(58) Field of Search ........................... 606/92, 94, 184, 606/167, 179, 190, 165, 165.02, 181; 600/204; 623/17.16, 17.12

(56) References Cited

U.S. PATENT DOCUMENTS

| | | | |
|---|---|---|---|
| 3,577,979 A | * | 5/1971 | van der Gaast ............. 600/567 |
| 4,265,618 A | | 5/1981 | Herskovitz et al. |
| 4,543,966 A | * | 10/1985 | Islam et al. ................. 600/567 |
| 4,793,363 A | * | 12/1988 | Ausherman et al. ........ 600/567 |
| 4,969,888 A | * | 11/1990 | Scholten et al. .............. 606/60 |
| 5,059,193 A | * | 10/1991 | Kuslich ........................ 606/60 |
| 5,549,679 A | * | 8/1996 | Kuslich ........................ 606/61 |
| 5,571,189 A | | 11/1996 | Kuslich |
| 5,630,826 A | * | 5/1997 | Sastri .......................... 606/170 |
| 6,238,407 B1 | * | 5/2001 | Wolf et al. .................. 606/185 |
| 6,368,337 B1 | * | 4/2002 | Kieturakis et al. .......... 600/207 |

OTHER PUBLICATIONS

Gokaslan, Ziya L. et al., *Contemporary Management of Spinal Cord Injury*, "Surgical Techniques: Thoracic and Lumbar", pp. 153–166 (at least as early as Apr. 28, 1999).
"Bone Marrow Biopsy/Aspiration Diamond Cut™ Needle", Information Sheet from Medical Biopsy, Inc., (at least as early as Apr. 28, 1999).

* cited by examiner

*Primary Examiner*—Michael J. Milano
*Assistant Examiner*—Gwen Phanijphand
(74) *Attorney, Agent, or Firm*—Sonnenschein Nath & Rosenthal

(57) ABSTRACT

Apparatus for injecting an immobilizing substance into a target site of a bone. The apparatus includes a cannula having a bore for transporting the immobilizing substance to the target site of the bone when a leading end of the cannula is positioned adjacent the target site of the bone. The bore has a diameter of at least about three millimeters. In addition, the apparatus includes a rotary cutter element removably attachable to the cannula for easing insertion of the cannula into position so the leading end of the cannula is positioned adjacent the target site of the bone and a connector attached to at least one of the cannula and the cutter element for releasably connecting the cutter element to the cannula during insertion of the cannula into position adjacent the target site of the bone. The apparatus also includes a handle attached to the cutter element for turning the cutter element to advance the leading end of the cannula into position adjacent the target site of the bone.

15 Claims, 16 Drawing Sheets

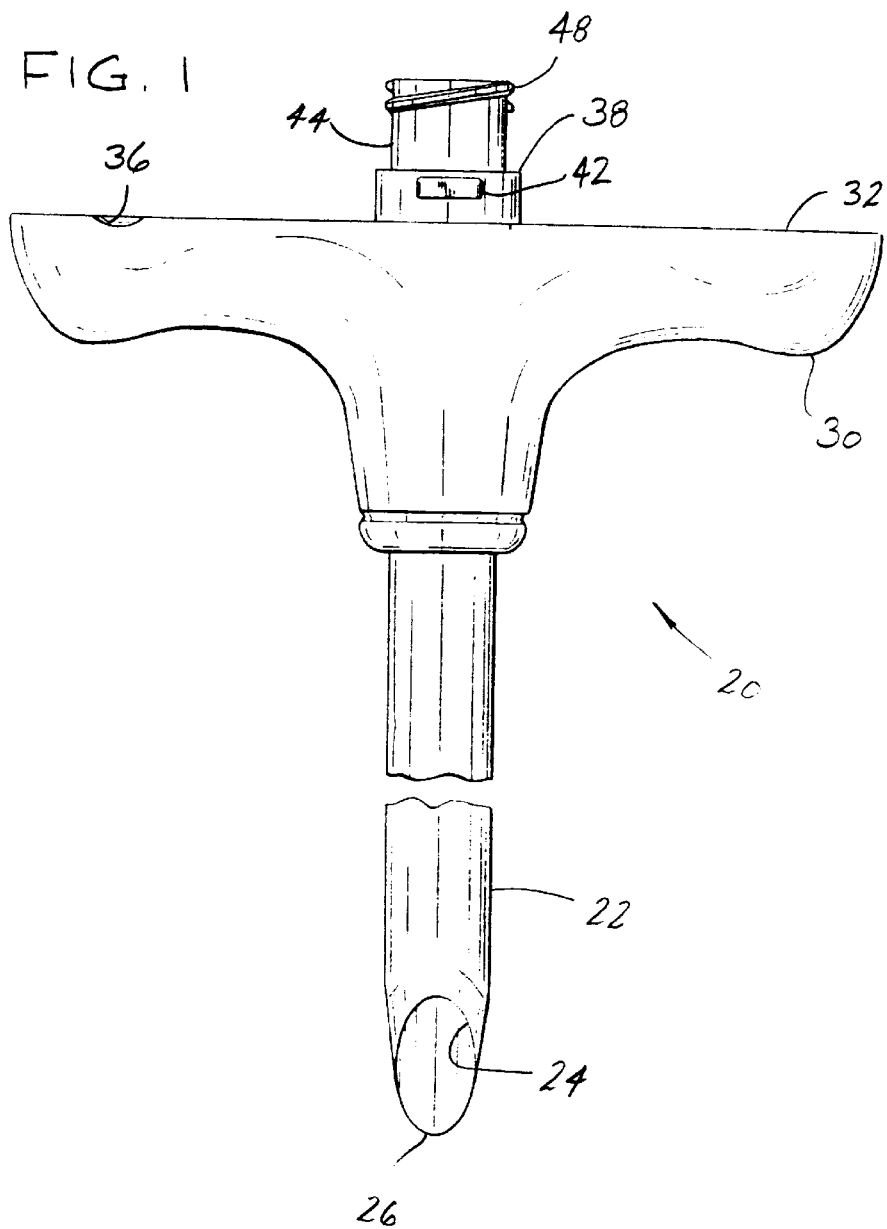
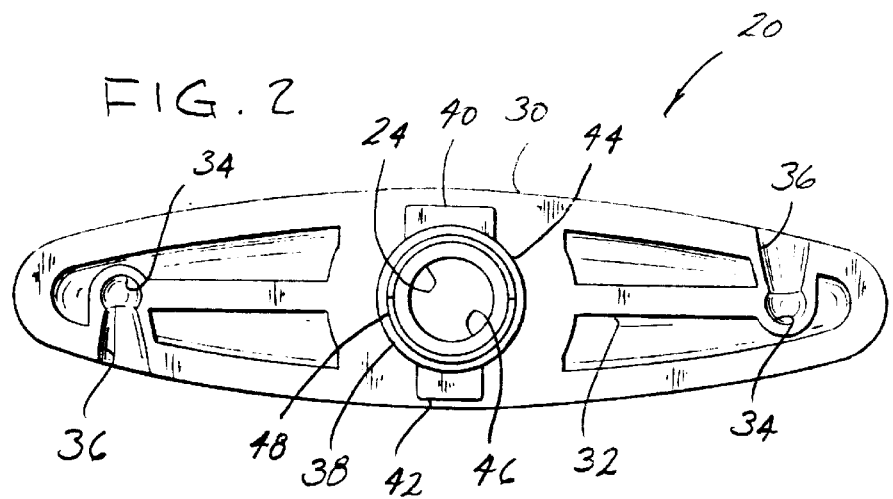

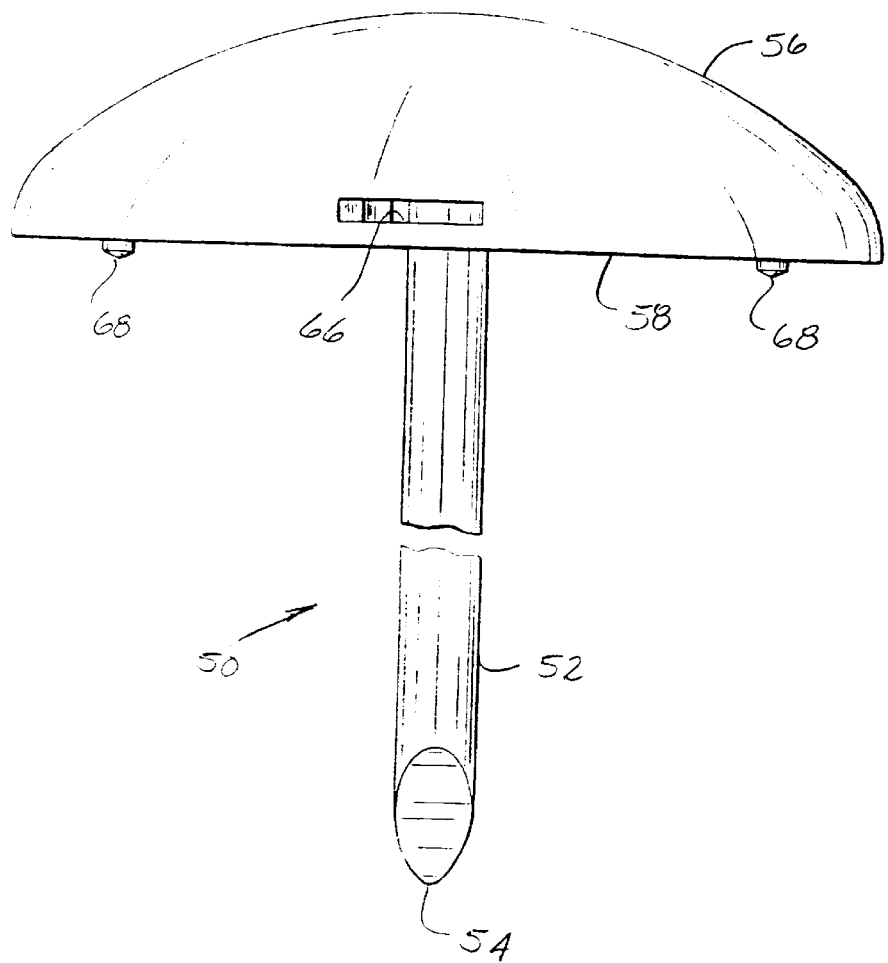
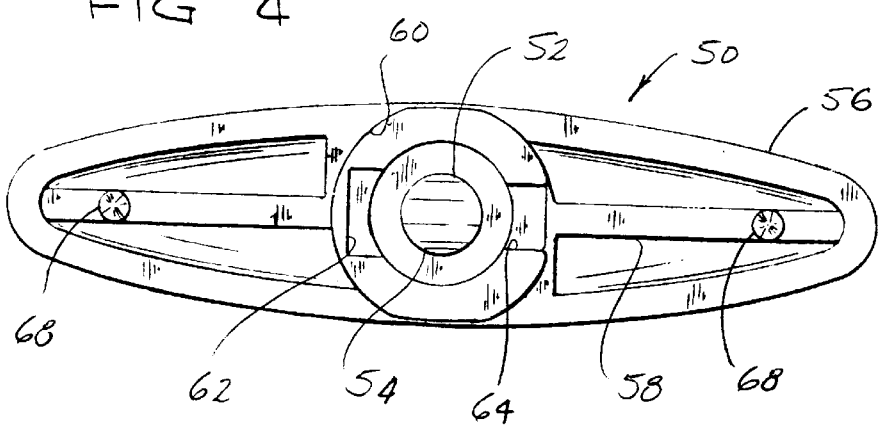

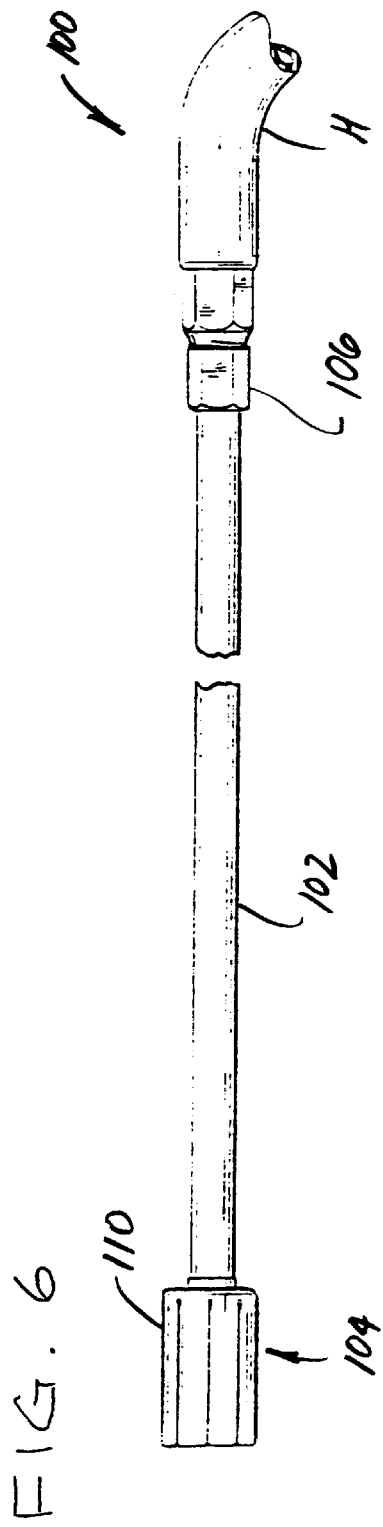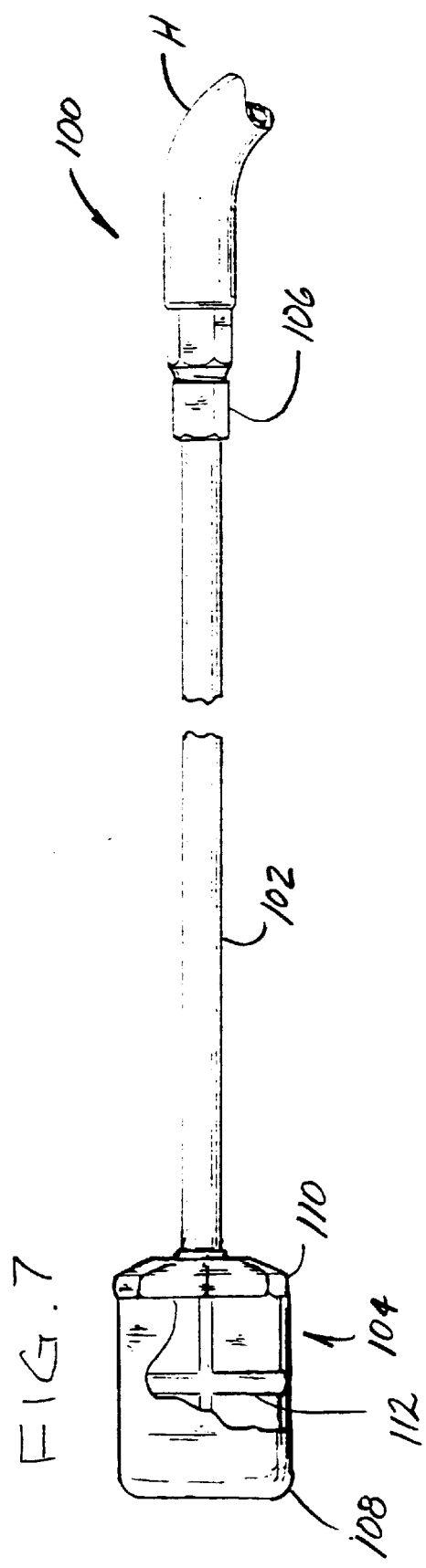

METHOD AND APPARATUS FOR PERCUTANEOUS OSTEOPLASTY

This application is a U.S. Formal based on Ser. No. 60/132,852, filed May 6, 1999.

BACKGROUND OF THE INVENTION

The present invention relates generally to osteoplasty and more particularly to a method and apparatus for introducing an immobilizing substance to a target site of a bone such as a vertebra to stabilize and repair fractures and the like in the bone.

Certain bone fractures, such as compressive fractures in vertebrae, frequently are unstable resulting in movement of fragments and pain. Such fractures typically are treated using open surgical procedures. Although these procedures vary, they generally require exposing the vertebra to remove the damaged bone and adjacent discs. Bone graft material or metal prostheses are introduced between the adjacent undamaged vertebrae after the bone and discs are removed. Plastic cement or harvested bone may also be introduced between the vertebrae to immobilize them and promote bone growth.

However, open surgical procedures cause significant trauma to surrounding tissue and increase the risk of complications such as infection compared to percutaneous techniques in which only a narrow instrument is inserted through the skin and soft tissue. Further, percutaneous techniques have the advantage of reducing the duration of both surgery and recovery times compared to open surgical procedures.

SUMMARY OF THE INVENTION

Among the several objects and features of the present invention may be noted the provision of a method and apparatus for repairing bone fractures, the provision of a method and apparatus which support and immobilize the bone, the provision of a method and apparatus which reduce trauma to surrounding tissue, the provision of a method and apparatus which reduce associated complications, and the provision of a method and apparatus which reduce surgery and recovery times.

Briefly, apparatus of this invention injects an immobilizing substance into a target site of a bone. The apparatus comprises a cannula having a bore for transporting the immobilizing substance to the target site of the bone when a leading end of the cannula is positioned adjacent the target site of the bone. The bore has a diameter of at least about three millimeters. In addition, the apparatus comprises a rotary cutter element removably attachable to the cannula for easing insertion of the cannula into position so the leading end of the cannula is positioned adjacent the target site of the bone and a connector attached to at least one of the cannula and the cutter element for releasably connecting the cutter element to the cannula during insertion of the cannula into position adjacent the target site of the bone. The apparatus also includes a handle attached to the cutter element for turning the cutter element to advance the leading end of the cannula into position adjacent the target site of the bone.

In another aspect, apparatus of this invention moves tissue away from a target site of a bone. The apparatus comprises a cannula having a bore extending through the cannula to a leading end positionable adjacent the target site of the bone and a tissue distraction device having a spreader mechanism adapted to move between a collapsed configuration in which the mechanism is sized and shaped to pass through the bore of the cannula and past the leading end to the target site and a deployed configuration in which the mechanism is enlarged thereby to move surrounding tissue away from the target site of the bone.

In yet another aspect, the present invention includes a method of injecting an immobilizing substance into a target site of a bone comprising the steps of connecting a cutter element to a cannula, rotating the cutter element and cannula to insert the cannula into position adjacent the target site of the bone, and removing the cutter element from the cannula. In addition, the method includes the step of inserting a tissue distraction device into the cannula. The tissue distraction device has a spreader mechanism for moving surrounding tissue away from the target site. Further, the method includes the steps of expanding the spreader mechanism to move the tissue away from the target site and injecting the immobilizing substance through the cannula to the target site.

Other objects and features of the present invention will be in part apparent and in part pointed out hereinafter.

BRIEF DESCRIPTION OF THE DRAWINGS

FIG. 1 is an elevation of a cannula of the present invention;

FIG. 2 is a top plan of the cannula;

FIG. 3 is an elevation of a rotary cutter element of the present invention;

FIG. 4 is a bottom plan of the rotary cutter element;

FIG. 6 is an elevation of a tissue distraction device showing a spreader mechanism in a collapsed position;

FIG. 7 is an elevation of the tissue distraction device showing the spreader mechanism in a deployed position;

Corresponding reference characters indicate corresponding parts throughout the several views of the drawings.

DETAILED DESCRIPTION OF THE PREFERRED EMBODIMENT

Figure 9:
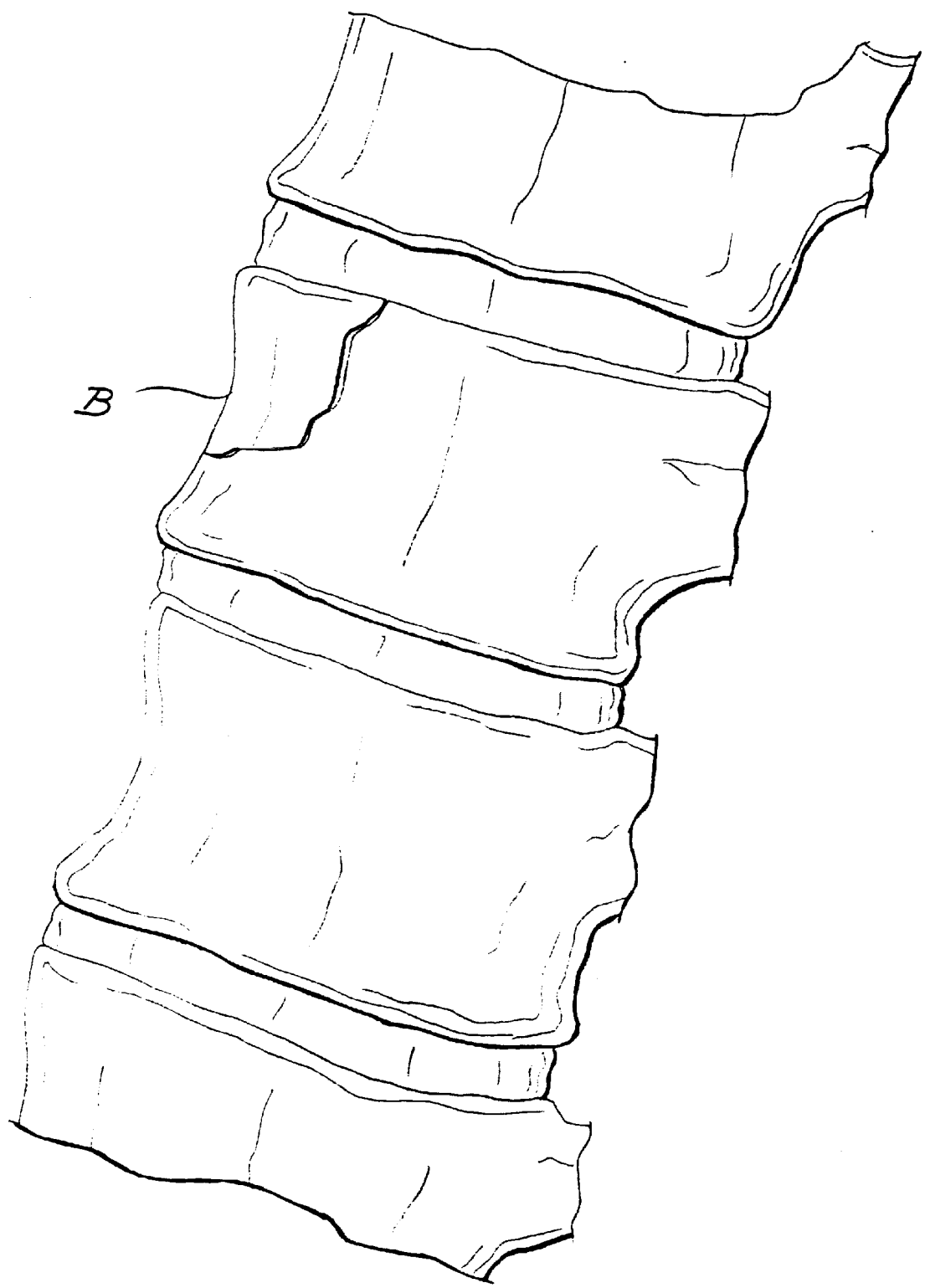
FIG. 9 is a side elevation of a portion of spine having a fractured vertebra.

Referring now to the drawings and in particular to FIG. 1, a cannula is generally designated by the reference numeral 20. The cannula 20 comprises a rigid tube 22 having a bore 24 for transporting an immobilizing substance S (FIG. 15) to a target site, generally designated by T (FIG. 10) of a bone B (FIG. 9). Although it is envisioned that the bore 24 may have other diameters without departing from the scope of the present invention, the bore of the preferred embodiment has a diameter of at least about three millimeters to permit viscous immobilizing substances S to easily pass through the bore. As will be understood by those skilled in the art, it is also desirable to minimize the diameter of the tube 22 to reduce trauma to tissue and bone B as the cannula 20 is inserted into the bone. Preferably, the diameter of the bore is between about four millimeters and about five millimeters. The bore 24 is coated with a non-reactive coating (not shown) such as Teflon® polymer or polyethylene to prevent the immobilizing substance S from contacting the tube 22, thereby preventing a chemical reaction between the immobilizing substance and the bore. Teflon is a U.S. federally registered trademark of E.I. du Pont de Nemours and Company of Wilmington, Del. The cannula tube 22 has a leading end 26 which is positioned adjacent the target site T of the bone B when transporting the immobilizing substance S to the bone. Although the leading end 26 of the preferred embodiment is tapered for easing insertion of the cannula 20 into position, leading ends having other shapes such as blunt or serrated are also envisioned as being within the scope of the present invention. In an alternate embodiment (not shown), the tube may have openings extending radially through the sides of the tube for delivering immobilizing substance S through the openings.

A T-grip handle half 30 is attached to the tube 22 opposite the leading end 26 for manipulating the leading end of the cannula into position adjacent the target site T of the bone B. The handle half 30 includes an elongate, rearward-facing surface 32 having a dimple 34 at each end. A ramp 36 extends from each dimple to an edge of the surface 32 as illustrated in FIG. 2. A male bayonet connector element 38 having opposite large and small lugs 40, 42, respectively, extends rearward from the surface 32 and a tubular extension 44 having an interior passage 46 and external threads 48 extends rearward from the bayonet connector element 38. Although the cannula 20 may be made from other materials without departing from the scope of the present invention, the tube 22 of the preferred embodiment is made from surgical steel and the handle half 30 is molded from plastic.

As illustrated in FIG. 3, a cutting element, generally designated by 50, is provided for easing insertion of the cannula into position so the leading end 26 is positioned adjacent the target site T of the bone B. The cutting element 50 includes a stylet 52 having a rotary cutting tip 54. The stylet 52 is a rigid rod sized and shaped for insertion through the bore 24 of the cannula 20 so the cutting tip 54 protrudes through the leading end 26 of the cannula for cutting the bone B and surrounding tissue (not shown) as the stylet is rotated. In the preferred embodiment, the stylet 52 has a diameter slightly less (e.g., 0.05 millimeter less) than the diameter of the bore 24 of the cannula 20 so tissue does not travel upward between the tube 22 of the cannula and the stylet 52 as the cannula and cutting tip are pushed into the tissue.

A second T-grip handle half 56 is attached to the cutter element 50 opposite the cutting tip 54 for turning the cutter element to advance it into position adjacent the target site T of the bone B. The second handle half 56 has a forward facing surface 58 which includes a centrally-located opening 60 for receiving the male bayonet connector 38 and the threaded tubular extension 44 when the stylet 52 is inserted through the bore 24 of the cannula 20. As shown in FIG. 4, the opening 60 includes opposite large and small rectangular notches 62, 64, respectively, for receiving the large and small lugs 40, 42 of the male bayonet connector 38 to releasably connect the stylet 52 to the cannula 20. As shown in FIG. 3, slots 66 are provided on each side of the handle half 56 (only one of which is visible in FIG. 3) for receiving the lugs 40, 42 when the stylet 52 is rotated relative to the cannula 20 for releasably connecting the cutting element 50 to the cannula, thereby preventing the stylet from being withdrawn from the cannula without first rotating the stylet to disconnect the bayonet connector. Although the bayonet connector may be configured differently without departing from the scope of the present invention, the connector of the preferred embodiment is configured so the stylet 52 rotates one quarter turn clockwise relative to the cannula 20 (when viewed from the rearward end) to connect the stylet to the cannula. Protrusions 68 extend forward from the forward facing surface 58 for engaging the dimples 34 at opposite ends of the first handle half 30 to deter rotation of the stylet 52 relative to the cannula 20 when the bayonet features are engaged. Although the stylet 52 may be made from other materials without departing from the scope of the present invention, the stylet 52 of the preferred embodiment is made from surgical steel and the handle half 56 is molded from plastic.

As will be appreciated by those skilled in the art, the large and small lugs and mating large and small notches permit the cannula 20 and stylet 52 to be assembled in only one way. Because the cutting tip 54 of the stylet 52 and the leading end 26 of the cannula 20 are both slanted, the lugs and notches ensure that the slanted ends are aligned with respect to one another when the cutter element 50 is attached to the cannula 20.

Figure 5:
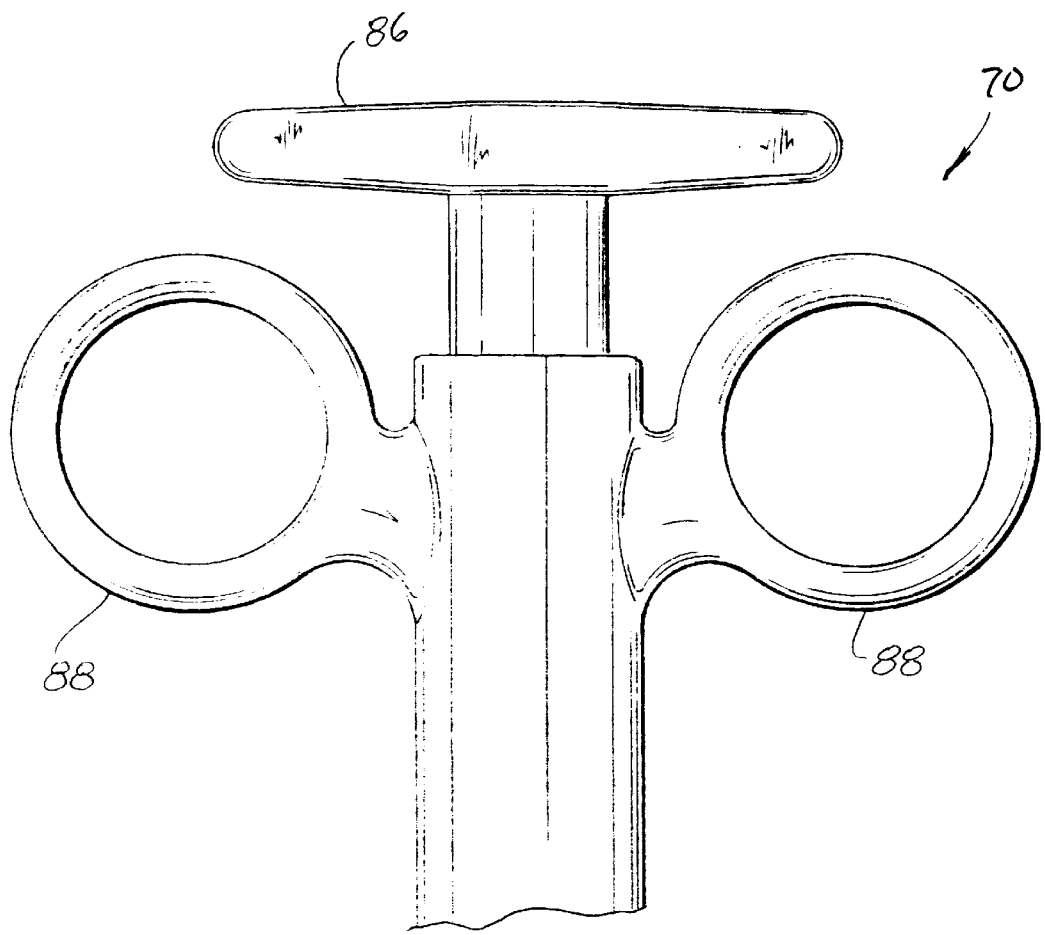
FIG. 5 is an elevation of a syringe of the present invention.

Referring to FIG. 5, a syringe for injecting the immobilizing substance S through the cannula 20 to the target site T of the bone B is generally designated by 70. The syringe 70 comprises a hollow cylinder 72 and a plunger 74. A nozzle 76 at one end of the cylinder 72 dispenses an immobilizing substance S (FIG. 15) through the nozzle 76 as the plunger 74 advances through the cylinder toward the nozzle. Although the nozzle 76 may have other inner diameters without departing from the scope of the present invention, the nozzle of the preferred embodiment has a diameter no smaller than the bore 24 of the cannula tube 22 to maintain low fluid resistance. The exterior surface of the nozzle 76 tapers for providing a fluid tight connection when the nozzle is forced into the interior passage 46 of the tubular extension 44 of the cannula 20. A collar 78 surrounding the nozzle 76 includes internal threads 80 for engaging the external threads 48 on the tubular extension 44 of the cannula 20 to releasably connect the syringe 70 to the cannula. As the syringe 70 is rotated to engage the respective threads of the syringe and cannula 20, the nozzle 76 is pushed into the internal passage 46 to ensure a fluid tight connection. Conversely, when the syringe 70 is rotated to disengage the threads, the nozzle 76 is pulled out of the internal passage 46 to permit easy separation of the syringe from the cannula 20.

As illustrated in FIG. 5, the cylinder 72 and plunger 74 have mating threads 82, 84, respectively, for moving the plunger toward the nozzle 76 to push the immobilizing substance S through the nozzle as the plunger is rotated relative to the cylinder. The plunger 74 includes a T-shaped handle 86 for facilitating rotation of the plunger. Finger rings 88 extending outward from opposite sides of the cylinder 72 also provide leverage to hold the cylinder and manipulate the syringe 70 into position. In an alternate embodiment (not shown), the mating threads 82, 84 of the plunger 74 and cylinder 72 may be omitted and the plunger may simply be advanced toward the nozzle 76 by pushing the plunger. It is also envisioned that other conventional mechanisms may be used to advance the plunger 74 toward the nozzle 76. Graduations 90 are provided at intervals along the cylinder 72 for determining the amount of immobilizing substance S contained in the syringe and assessing the amount of substance previously injected.

A temporary filling tip 92 is shown installed on the syringe 70 in FIG. 5 for use when filling the syringe 70 to prevent the immobilizing substance from contacting the internal threads 80 of the syringe or the exterior surface of the syringe nozzle 76. The tip 92 eliminates the need to clean the nozzle and threads before connecting the syringe to the cannula 20. External threads 94 provided on the tip 92 are adapted to engage the internal threads 80 of the syringe 70 for releasably connecting the tip to the syringe.

A tissue distraction device is generally designated by 100 in FIGS. 6 and 7. The distraction device 100 includes a hollow tube 102 and a spreader mechanism, generally designated by 104, adapted to move between a collapsed configuration as shown in FIG. 6 in which the mechanism is sized and shaped to pass through the bore 24 of the cannula 20 and a deployed configuration as shown in FIG. 7 in which the mechanism is expanded. As illustrated in FIG. 7, the tube 102 includes a conventional fastener 106 for attaching the device 100 to a hose H connected to a pressurized air supply (not shown). The spreader mechanism 104 includes an expandable bladder 108 attached to the tube 102 opposite the fastener 106. The bladder 108 may be selectively filled with air from the pressurized air source to expand the bladder to the deployed configuration to move surrounding tissue away from the target site T of the bone B. A protective sheath 110 which collapses to the configuration shown in FIG. 6 for passing through the bore 24 prevents the bladder 108 from contacting the leading end 26 of the cannula 20 thereby protecting the bladder from puncture. Once past the leading end 26 of the cannula 20, the protective sheath 110 fans outward as shown in FIG. 7 under the influence of pressure from the expanding bladder 108. The spreader mechanism 104 also includes a collapsible resilient cage 112 positioned inside the bladder 108 to shape the bladder when expanded. Depending upon the size, shape and location of the fracture, cages having different sizes and shapes may be desirable.

Figure 8:
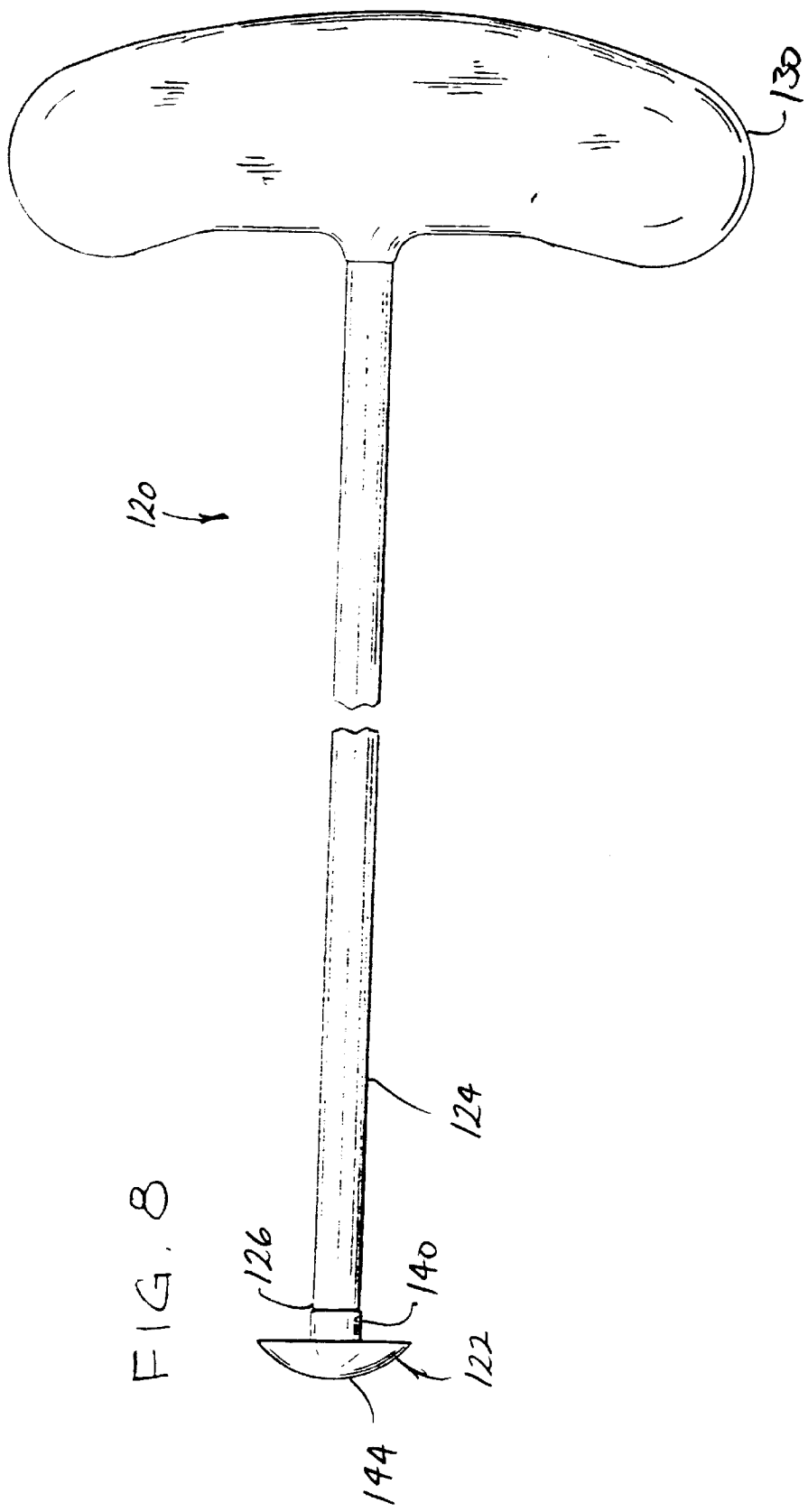
FIG. 8 is an elevation of a plug and apparatus for introducing the plug.

As illustrated in FIG. 8, a positioning device, generally designated by 120, is used to position a plug, generally designated by 122, at a selected site X (FIG. 19) adjacent the target site T of the bone B for retaining the immobilizing substance S at the target site of the bone. The positioning device 120 includes a stem 124 sized and shaped for insertion through the bore 24 of the cannula 20 so a forward end 126 of the stem protrudes through the leading end 26 of the cannula. The forward end 126 of the stem 124 is adapted to releasably engage the plug 122 for pushing the plug through the bore 24 of the cannula 20 and deploying it at the selected site X adjacent the target site T of the bone B. Although other means may be used to releasably engage the plug 122, in the most preferred embodiment the forward end 126 of the stem 124 has screw threads 128 (FIG. 17) which releasably engage the plug. A T-shaped grip 130 is provided on the stem 124 opposite the forward end 126 for manipulating the plug 122 through the bore 24 of the cannula 20.

As illustrated in FIG. 8, the plug 122 includes a hub 140 which has means, e.g., screw threads 142 (FIG. 17), for releasably receiving the forward end 126 of the stem 124 and a flexible head 142 for retaining the immobilizing substance S in position at the target site T. The head 142 is collapsible so it may be pushed through the bore 24 of the cannula 20 and resilient so it returns to its original shape shown in FIG. 8 to block flow through the opening O (FIG. 19) in the bone B created by the cannula when inserted through the bone.

Having explained the various surgical apparatus used for injecting an immobilizing substance S into a target site T of a bone B, the procedure for their use will now be described. Although the procedure may be performed on various bones such as long bones and vertebrae, the following description will be directed to the repair of a fractured vertebra. FIG. 9 illustrates a fracture F in a bone B prior to performing the procedure, and FIGS. 10–19 illustrate various steps of the procedure used to repair the bone. Before beginning the procedure, conventional pre-operative procedures such as cleaning surrounding skin will be performed and a local anesthetic will be administered.

Figure 10:
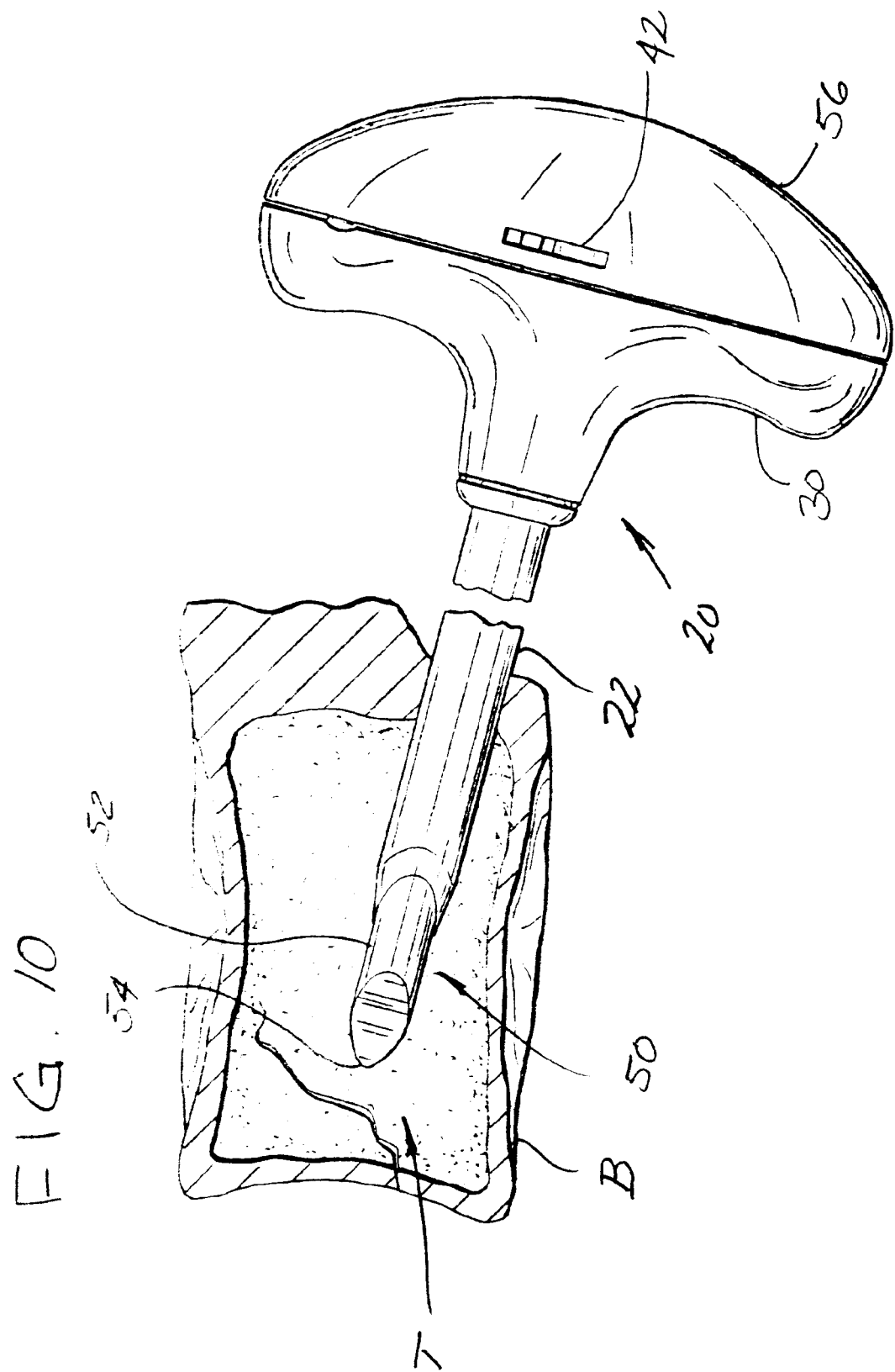
FIG. 10 is a section of the fractured vertebra showing the cannula and rotary cutter element inserted therein.
Figure 11:
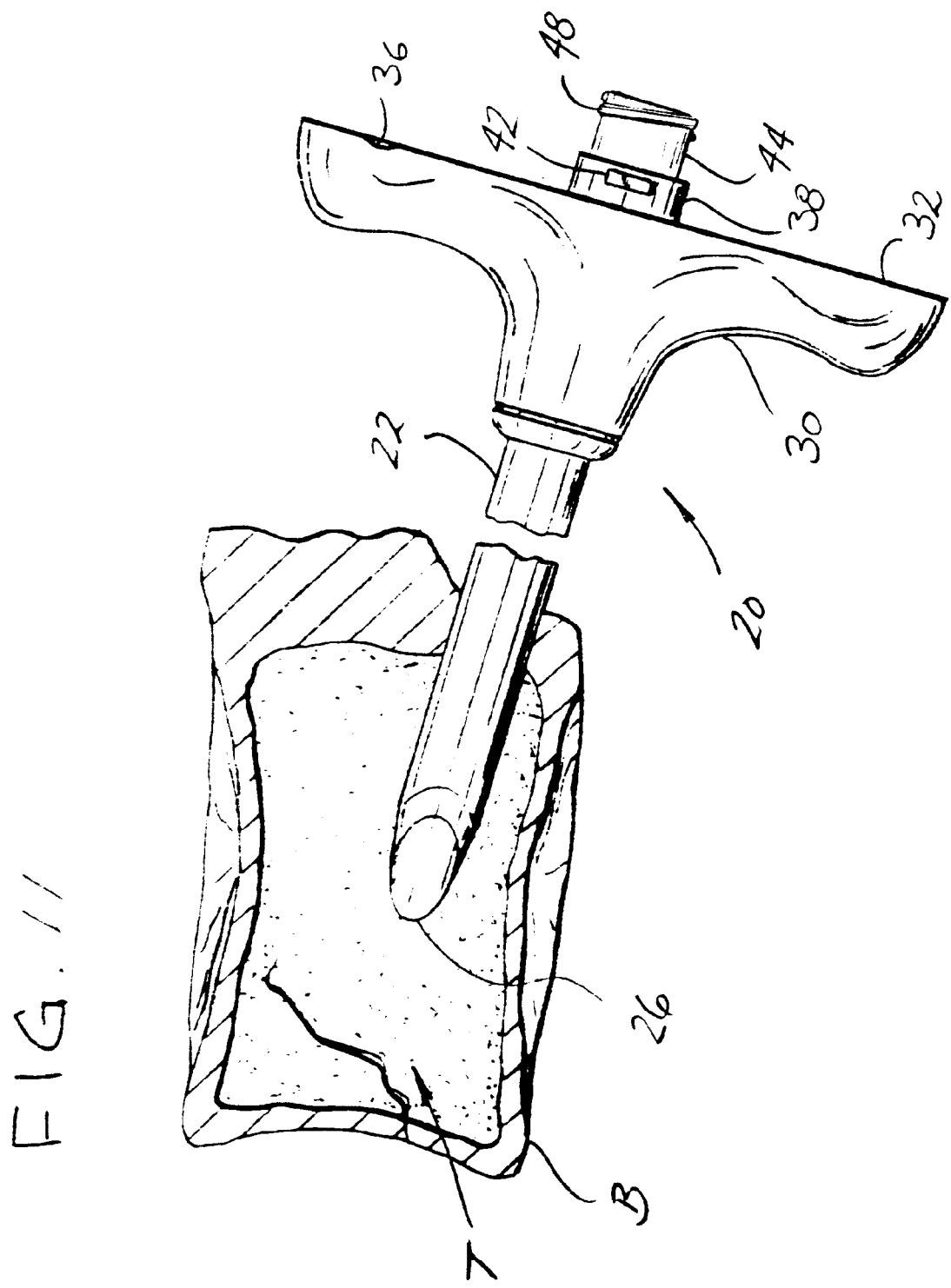
FIG. 11 is a section similar to FIG. 10 but showing the rotary cutter element removed from the cannula.

The cutter element 50 will be connected to the cannula 20 by sliding the stylet 52 of the cutter element into the bore 24 of the cannula, inserting the lugs 40, 42 of the cannula into the respective notches 62, 64 of the cutter element, and rotating the cutter element one quarter turn clockwise (as viewed from the rearward end) relative to the cannula to engage the bayonet connector. The surgeon will grasp the mating halves of the handle 30, 56 and simultaneously rotate the cutter element 50 and cannula 20 clockwise while guiding them through the tissue and into the bone B. The cutting tip 54 of the cutter element 50 will cut the tissue and bone B to ease insertion of the apparatus into position so the tip 26 of the cannula 20 is adjacent the target site T of the bone B as illustrated in FIG. 10. Image guided control such as fluoroscopy, computer tomography and/or stereoscopic image guidance may be used to position the apparatus. Once the apparatus is in position, the cutter element 50 will be removed from the cannula 20 as shown in FIG. 11 by rotating the cutter element one quarter turn counterclockwise (as viewed from the rearward end) relative to the cannula and withdrawing the stylet 52 from the bore 24 of the cannula.

Figure 12:
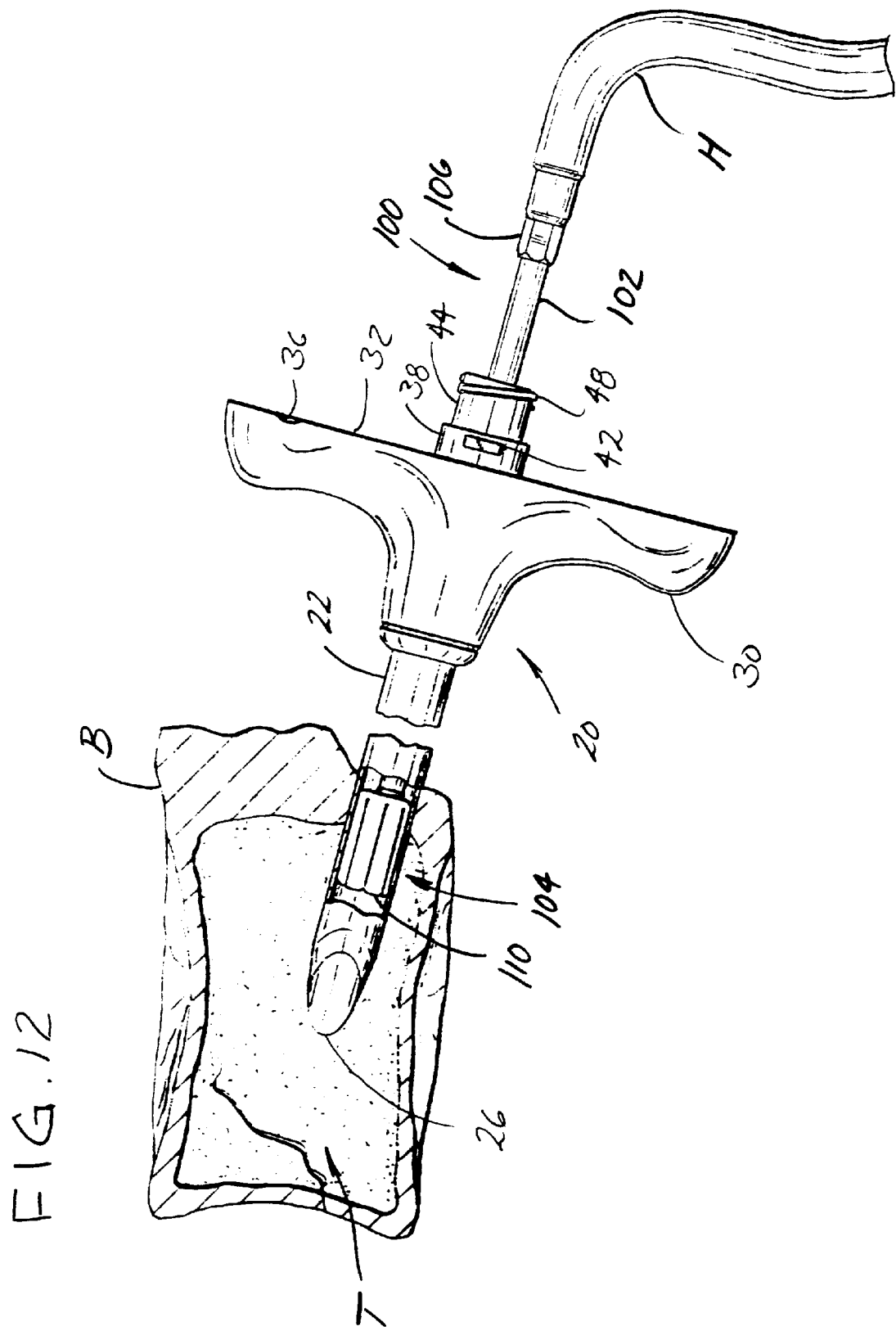
FIG. 12 is a section showing the tissue distraction device insert into the cannula.
Figure 13:
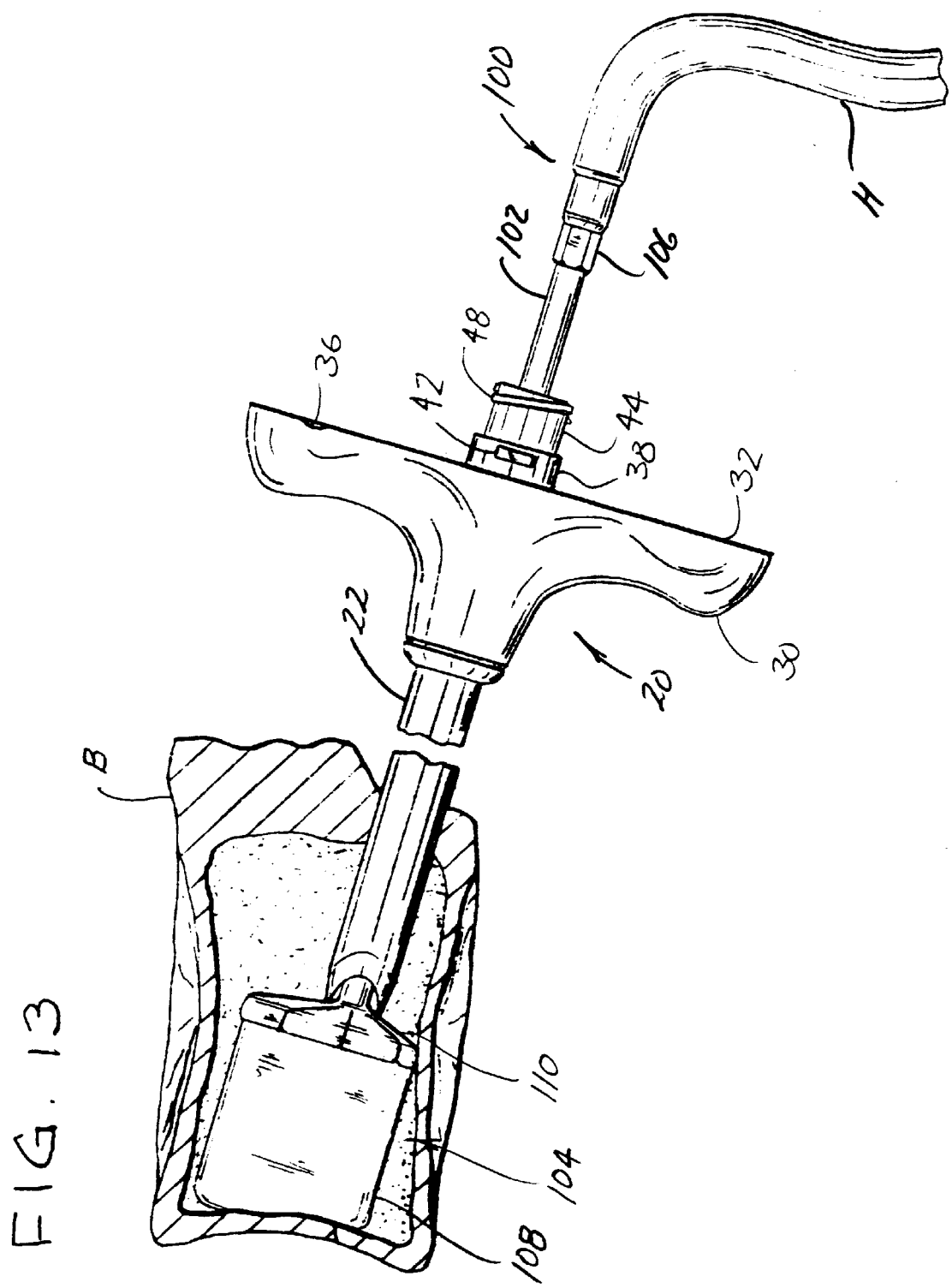
FIG. 13 is a section showing the spreader mechanism deployed inside the vertebra.
Figure 14:
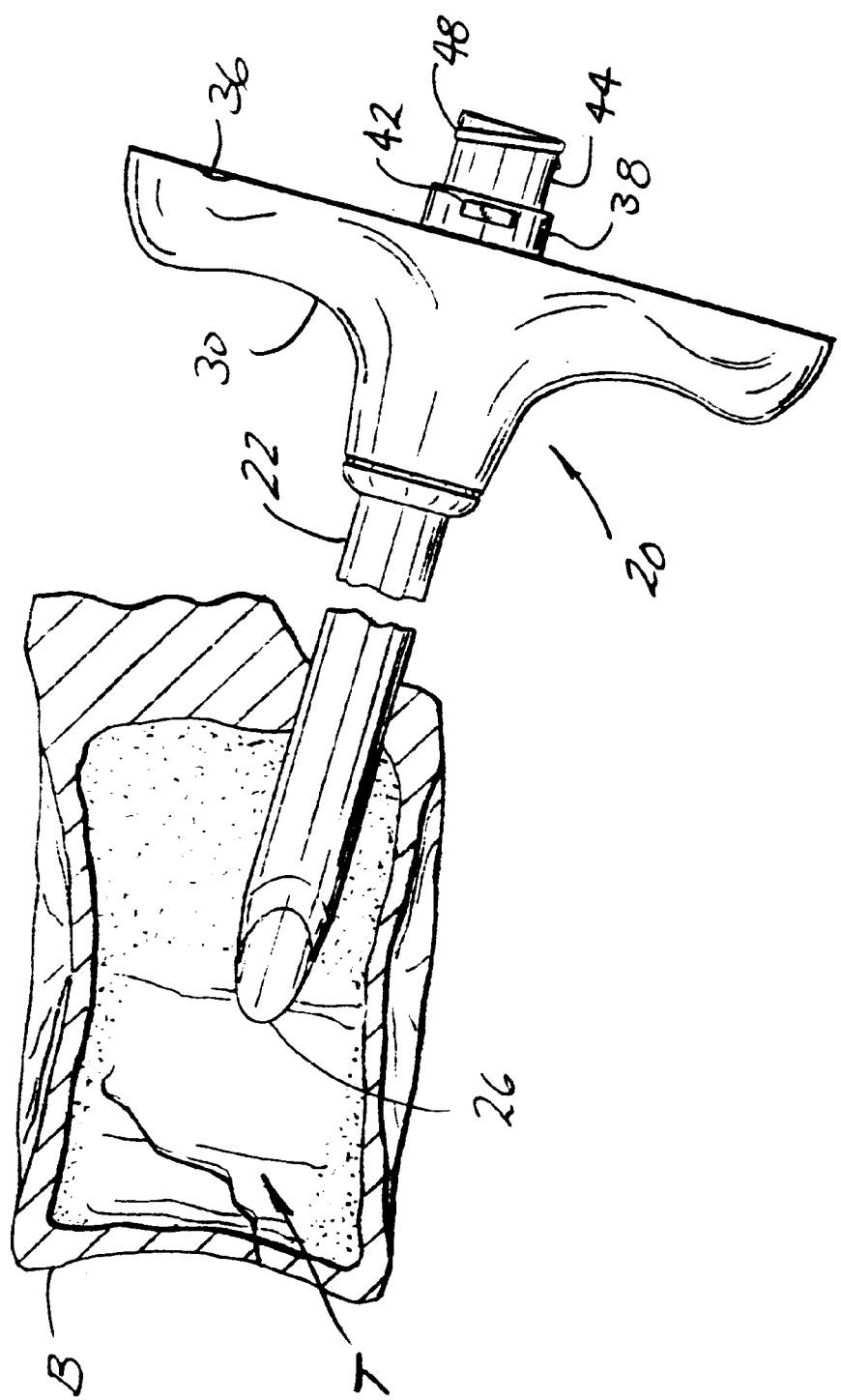
FIG. 14 is a section showing the spreader mechanism removed from the cannula.

Next, the tissue distraction device 100 will be connected to the hose H and guided through the bore 24 of the cannula 20 as shown in FIG. 12. Once the device 100 protrudes through the leading end 26 of the cannula 20, the bladder 108 will be expanded by pressurizing it with air. As the bladder 108 expands, the sheath 110 will open to the position shown in FIG. 13. Because the cage 112 inside the bladder 108 is resilient, the bladder will take on a predetermined shape, such as a rectangular solid, to move tissue and fragments away from the target site T of the bone B. The bladder 108 then will be deflated and retracted back through the bore 24 of the cannula 20, leaving a void at the target site T as shown in FIG. 14.

Figure 15:
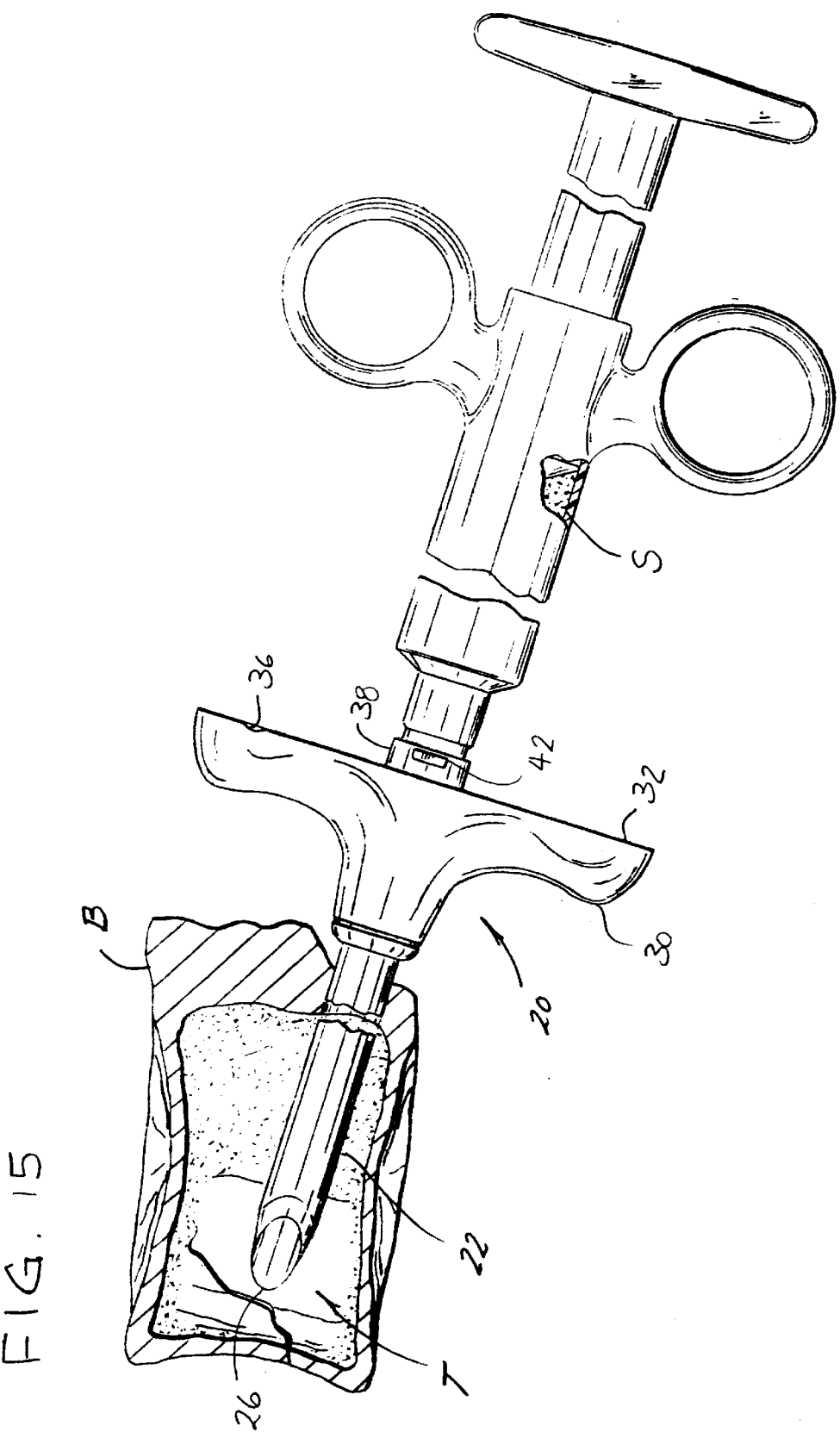
FIG. 15 is a section showing the syringe connected to the cannula.
Figure 16:
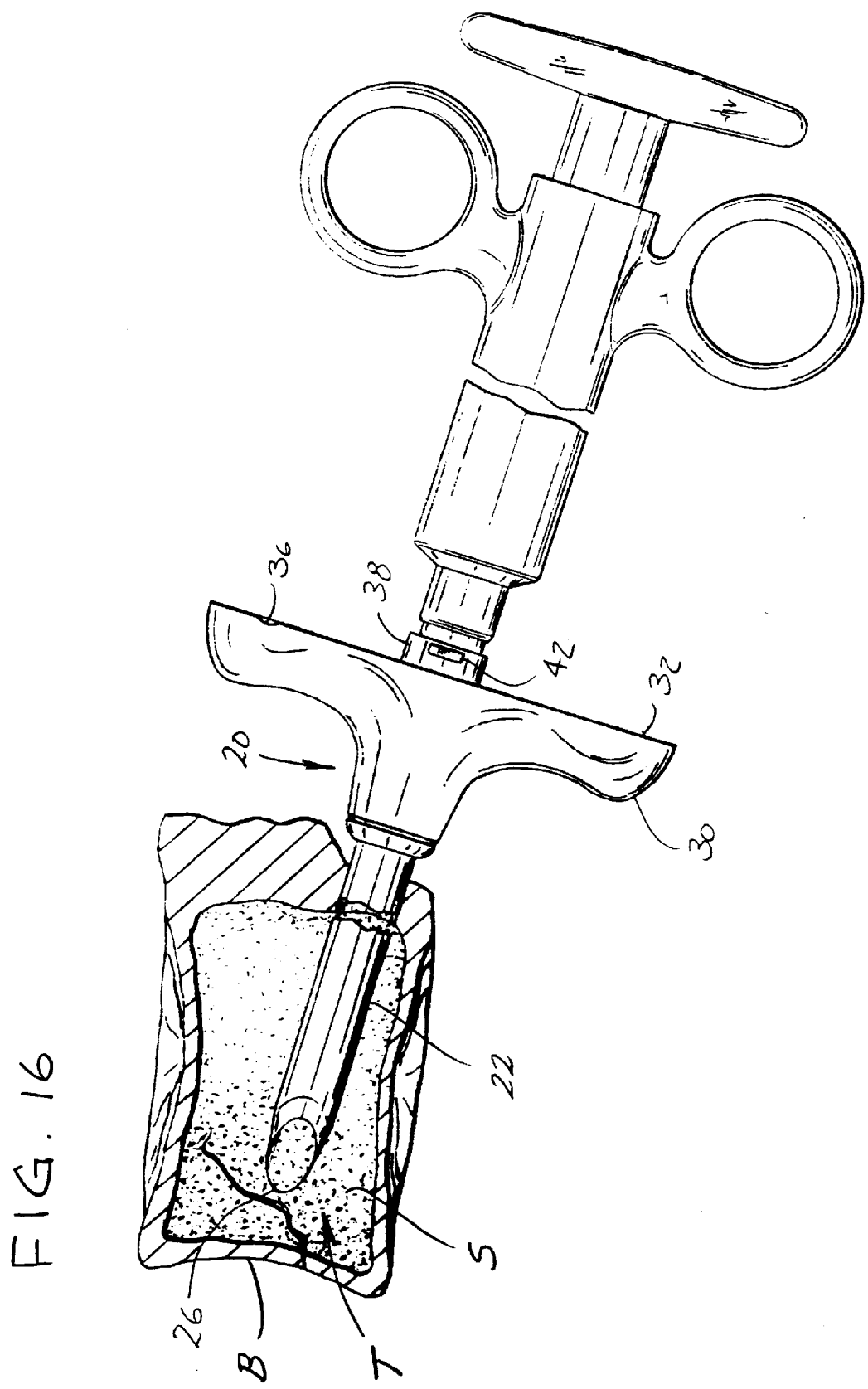
FIG. 16 is a section showing the syringe injecting an immobilizing substance through the cannula to a target site in the vertebra.
Figure 17:
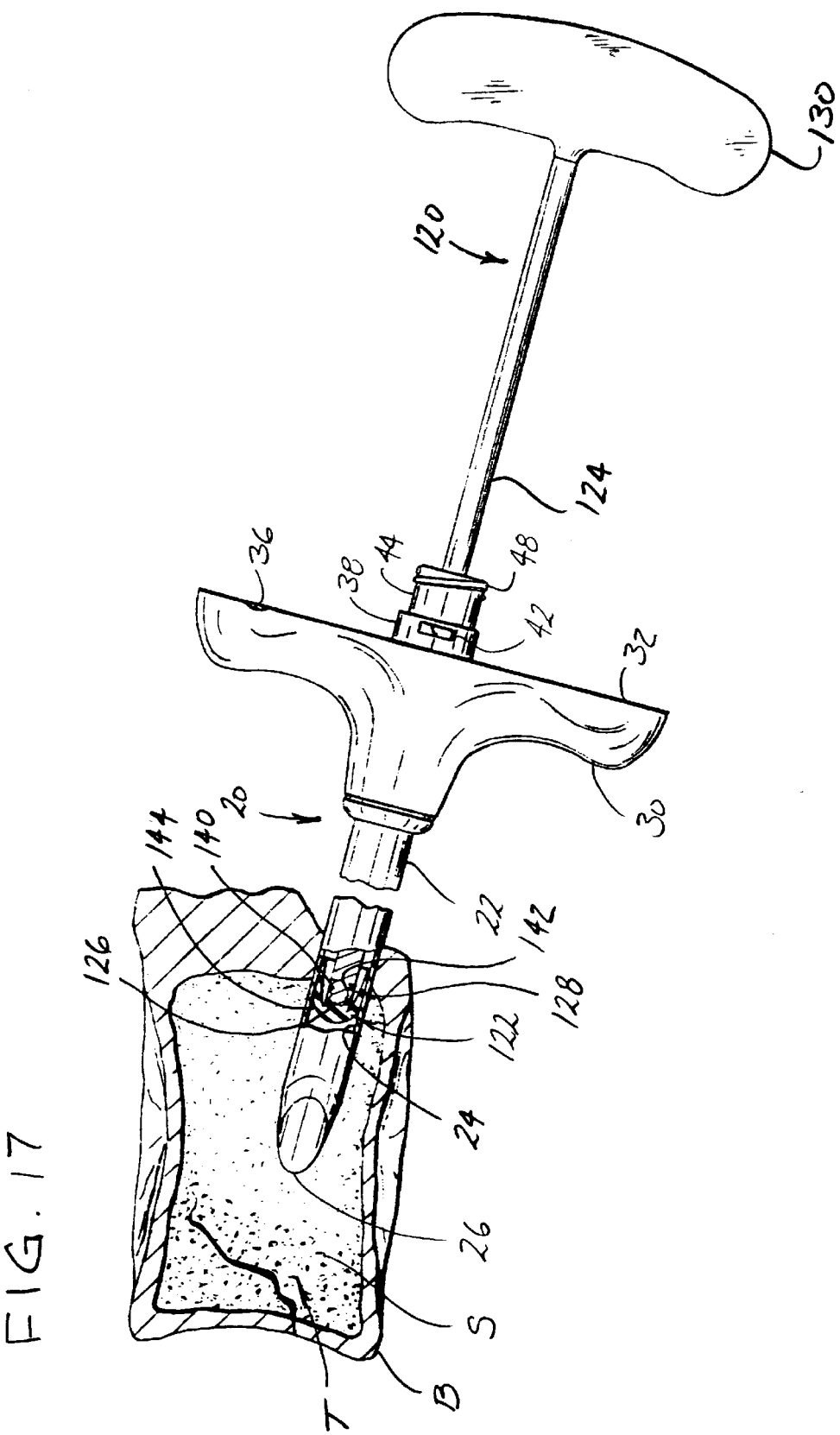
FIG. 17 is a section showing the plug being inserted through the cannula.
Figure 18:
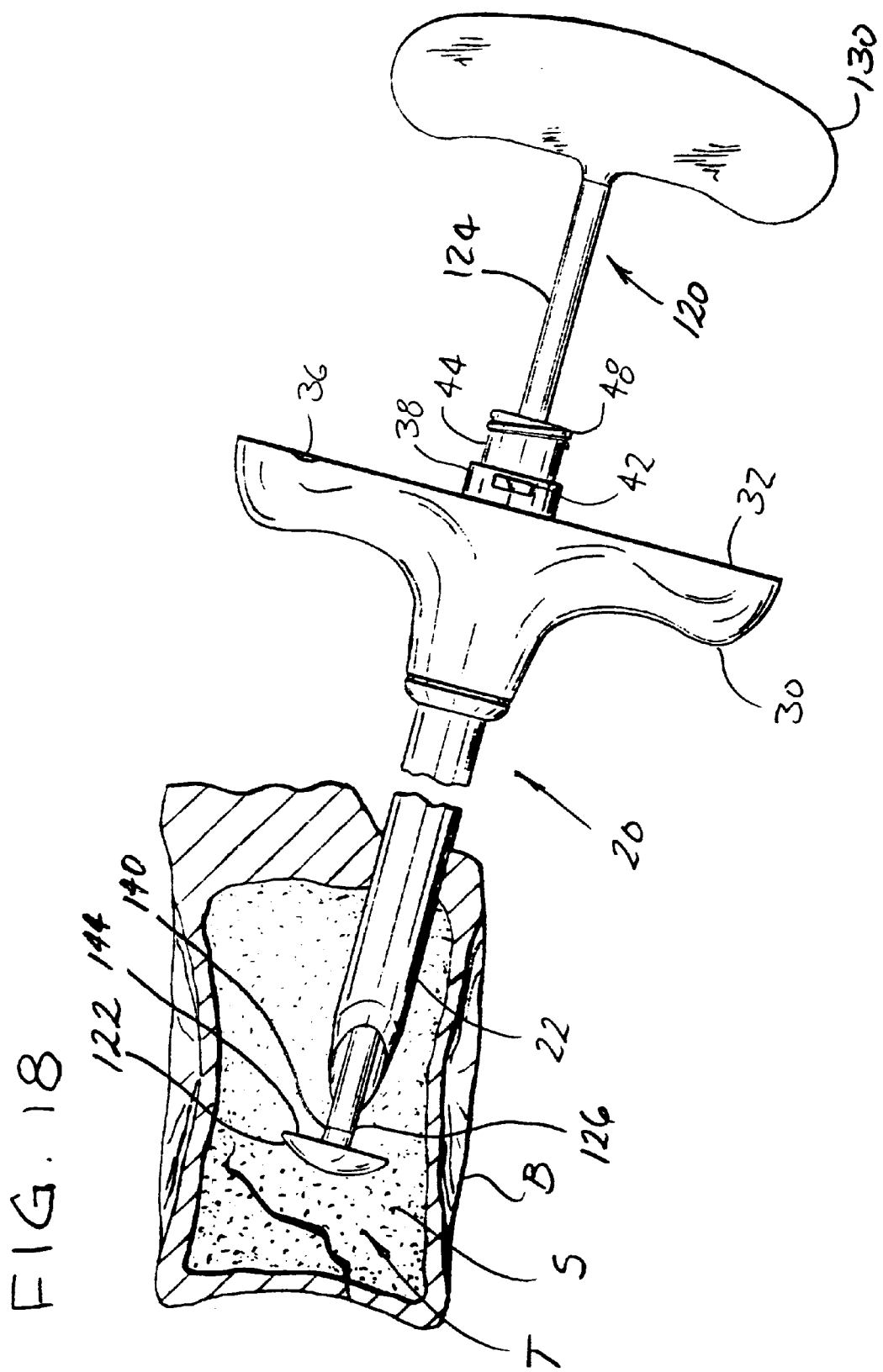
FIG. 18 is a section showing the plug protruding from the cannula.
Figure 19:
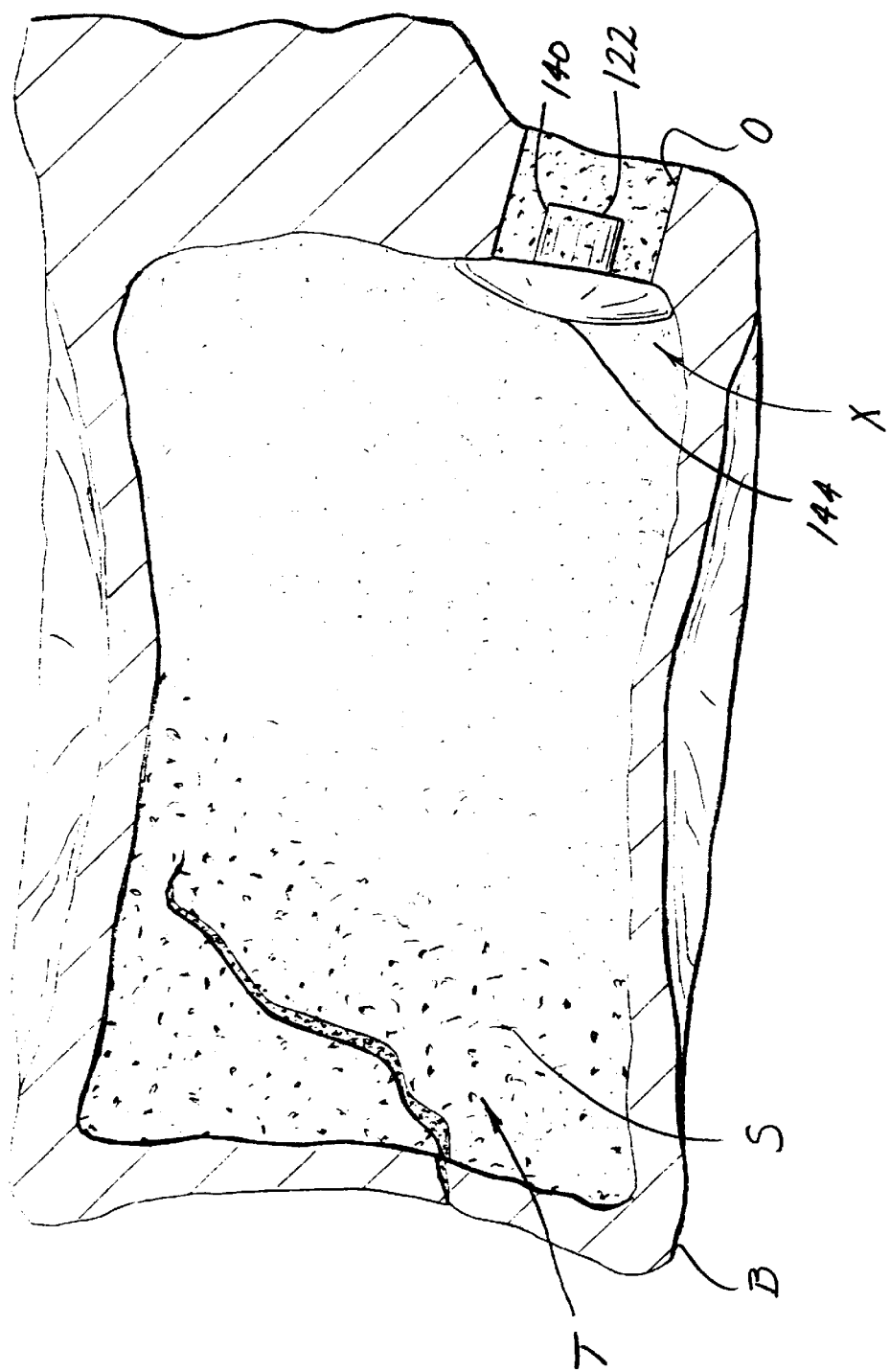
FIG. 19 is a section showing the plug installed in the vertebra for retaining the immobilizing substance at the target site in the vertebra.

Once the target site T is cleared of tissue, a syringe 70 filled with immobilizing substance S will be connected to the cannula 20 as shown in FIG. 15 by engaging the threads 80 of the syringe with the threads 48 on the cannula. The plunger 74 of the syringe 70 will be rotated relative to the cylinder 72 to inject the immobilizing substance S through the nozzle 76 of the syringe and the bore 24 of the cannula 20 to the target site T as shown in FIG. 16. Once a sufficient amount of immobilizing substance S is injected into the target site T, the syringe 70 will be removed from the cannula 20 by disengaging the mating threads, and the positioning device 120 and plug 122 will be inserted through the bore 24 of the cannula as shown in FIG. 17 until the head 144 of the plug protrudes through the leading end 26 of the cannula as shown in FIG. 18. The plug 122, positioning device 120 and cannula 20 will be slowly withdrawn until the head 144 of the plug contacts the bone B at a selected site X adjacent the target site T of the bone. The positioning device 120 will be disengaged from the plug 122 by rotating the device while gently pulling the device to keep the plug from turning. Once the plug 122 is disengaged, it will be left in place as shown in FIG. 19 to block flow through the opening 0 and retain the immobilizing substance S at the target site T of the bone B. The device 120 and cannula 20 will be withdrawn the rest of the way from the patient and the small hole in the tissue will be sutured to complete the procedure.

It is envisioned that the previously described apparatus and procedure may be used to inject an immobilizing substance such as methyl metacrylate or a bone growth promoting substance into the target site T of a bone B. Preferably the immobilizing substance or bone growth promoting substance will be liquid prior to curing so it can flow through the cannula 20 to the target site T of the bone B. After delivery to the target site T, the substances will polymerize and harden to immobilize the fracture, and to prevent movement of fragments which can cause collapse, deformity and pain. The procedure and apparatus described above cause very little trauma to surrounding tissue compared to conventional open surgery. As a result, the procedure and apparatus reduce associated complications, as well as surgical and recovery times.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for injecting an immobilizing substance into a target site of a bone comprising:
   a cannula having a bore for transporting the immobilizing substance to the target site of the bone when a leading end of the cannula is positioned adjacent the target site of the bone, the bore having a diameter of at least about three millimeters;
   a rotary cutter element removably attachable to the cannula for easing insertion of the cannula into position so the leading end of the cannula is positioned adjacent the target site of the bone;
   a connector attached to at least one of the cannula and the cutter element for releasably connecting the cutter element to the cannula during insertion of the cannula into position adjacent the target site of the bone;
   a handle attached to the cutter element for turning the cutter element to advance the leading end of the cannula into position adjacent the target site of the bone; and
   a syringe releasably connectable to the cannula for injecting the immobilizing substance through the bore of the cannula to the fractured bone.

2. Apparatus as set forth in claim 1 wherein the cutter element comprises a stylet having a rotary cutting tip, the stylet being sized and shaped for insertion through the bore of the cannula so the cutting tip protrudes through the leading end of the cannula for cutting the bone as the stylet is rotated to ease insertion of the cannula into position adjacent the target site of the bone.

3. Apparatus as set forth in claim 1 wherein the connector is a bayonet connector having mating halves, one of said halves being attached to the cannula and another of said halves being attached to the cutter element for releasably connecting the cutter element to the cannula during insertion of the cannula into position adjacent the target site of the bone.

4. Apparatus as set forth in claim 1 wherein the handle is a T-grip having mating halves, one of said halves being attached to the cannula and another of said halves being attached to the cutter element, the halves being adapted for alignment when the connector connects the cutter element to the cannula.

5. Apparatus as set forth in claim 1 further comprising a tissue distraction device having a spreader mechanism adapted to move between a collapsed configuration in which the mechanism is sized and shaped to pass through the bore of the cannula and past the leading end to the target site and a deployed configuration in which the mechanism is enlarged thereby to move surrounding tissue away from the target site of the bone.

6. Apparatus as set forth in claim 5 wherein the spreader mechanism of the tissue distraction device comprises an expandable bladder which is expandable to the deployed configuration by pressurizing the bladder to move surrounding tissue away from the target site of the bone.

7. Apparatus for injecting an immobilizing substance into a target site of a bone comprising:
   a cannula having an inner surface defining a bore for transporting the immobilizing substance to the target site of the bone when a leading end of the cannula is positioned adjacent the target site of the bone, the bore having a diameter of at least about three millimeters and a non-reactive coating to prevent the immobilizing substance from contacting the inner surface of the cannula, thereby preventing a chemical reaction between the immobilizing substance and the bore;
   a rotary cutter element removably attachable to the cannula for easing insertion of the cannula into position so the leading end of the cannula is positioned adjacent the target site of the bone;
   a connector attached to at least one of the cannula and the cutter element for releasably connecting the cutter element to the cannula during insertion of the cannula into position adjacent the target site of the bone; and
   a handle attached to the cutter element for turning the cutter element to advance the leading end of the cannula into position adjacent the target site of the bone.

8. Apparatus for injecting an immobilizing substance into a target site of a bone comprising:
   a cannula having a bore for transporting the immobilizing substance to the target site of the bone when a leading end of the cannula is positioned adjacent the target site of the bone, the bore having a diameter of at least about three millimeters;
   a rotary cutter element removably attachable to the cannula for easing insertion of the cannula into position so the leading end of the cannula is positioned adjacent the target site of the bone;
   a connector attached to at least one of the cannula and the cutter element for releasably connecting the cutter element to the cannula during insertion of the cannula into position adjacent the target site of the bone;
   a handle attached to the cutter element for turning the cutter element to advance the leading end of the cannula into position adjacent the target site of the bone; and a tissue distraction device having a spreader mechanism adapted to move between a collapsed configuration in which the mechanism is sized and shaped to pass through the bore of the cannula and past the leading end to the target site and a deployed configuration in which the mechanism is enlarged thereby to move surrounding tissue away from the target site of the bone, said spreader mechanism including an expandable bladder that is expandable to the deployed configuration by pressurizing the bladder to move surrounding tissue away from the target site of the bone and a protective sheath sized and shaped to pass through the bore and past the leading end of the cannula to prevent the bladder from contacting the leading end of the cannula.

9. Apparatus as set forth in claim 8 wherein the protective sheath is adapted to spread outward when extended past the leading end of the cannula.

10. Apparatus for injecting an immobilizing substance into a target site of a bone comprising:

a cannula having a bore for transporting the immobilizing substance to the target site of the bone when a leading end of the cannula is positioned adjacent the target site of the bone, the bore having a diameter of at least about three millimeters;

a rotary cutter element removably attachable to the cannula for easing insertion of the cannula into position so the leading end of the cannula is positioned adjacent the target site of the bone;

a connector attached to at least one of the cannula and the cutter element for releasably connecting the cutter element to the cannula during insertion of the cannula into position adjacent the target site of the bone;

a handle attached to the cutter element for turning the cutter element to advance the leading end of the cannula into position adjacent the target site of the bone; and a tissue distraction device having a spreader mechanism adapted to move between a collapsed configuration in which the mechanism is sized and shaped to pass through the bore of the cannula and past the leading end to the target site and a deployed configuration in which the mechanism is enlarged thereby to move surrounding tissue away from the target site of the bone, said spreader mechanism including an expandable bladder that is expandable to the deployed configuration by pressurizing the bladder to move surrounding tissue away from the target site of the bone and a collapsible cage positioned inside the bladder to shape the bladder when expanded.

11. Apparatus for injecting an immobilizing substance into a target site of a bone comprising:

a cannula having a bore for transporting the immobilizing substance to the target site of the bone when a leading end of the cannula is positioned adjacent the target site of the bone, the bore having a diameter of at least about three millimeters;

a rotary cutter element removably attachable to the cannula for easing insertion of the cannula into position so the leading end of the cannula is positioned adjacent the target site of the bone;

a connector attached to at least one of the cannula and the cutter element for releasably connecting the cutter element to the cannula during insertion of the cannula into position adjacent the target site of the bone;

a handle attached to the cutter element for turning the cutter element to advance the leading end of the cannula into position adjacent the target site of the bone; and a positioning device for positioning a plug at a selected site adjacent the target site of the bone for retaining the immobilizing substance at the target site of the bone, said positioning device comprising a stem sized and shaped for insertion through the bore of the cannula so an end of the stem protrudes through the leading end of the cannula, said end of the stem being adapted to releasably engage the plug to push the plug through the bore of the cannula and to deploy the plug at the selected site adjacent the target site of the bone.

12. Apparatus for moving tissue away from a target site of a bone comprising:

a cannula having a bore extending through the cannula to a leading end positionable adjacent the target site of the bone; and a tissue distraction device having a spreader mechanism adapted to move between a collapsed configuration in which the mechanism is sized and shaped to pass through the bore of the cannula and past the leading end to the target site and a deployed configuration in which the mechanism is enlarged thereby to move surrounding tissue away from the target site of the bone, said spreader mechanism including an expandable bladder that is expandable to the deployed configuration by pressurizing the bladder to move surrounding tissue away from the target site of the bone and a protective sheath sized and shaped to pass through the bore and past the leading end of the cannula to prevent the bladder from contacting the leading end of the cannula.

13. Apparatus as set forth in claim 12 wherein the protective sheath is adapted to spread outward when extended past the leading end of the cannula.

14. Apparatus for moving tissue away from a target site of a bone comprising:

a cannula having a bore extending through the cannula to a leading end positionable adjacent the target site of the bone; and a tissue distraction device having a spreader mechanism adapted to move between a collapsed configuration in which the mechanism is sized and shaped to pass through the bore of the cannula and past the leading end to the target site and a deployed configuration in which the mechanism is enlarged thereby to move surrounding tissue away from the target site of the bone, said spreader mechanism including an expandable bladder that is expandable to the deployed configuration by pressurizing the bladder to move surrounding tissue away from the target site of the bone and a collapsible cage positioned inside the bladder to shape the bladder when expanded.

15. A method of injecting an immobilizing substance into a target site of a bone comprising the steps of:

connecting a cutter element to a cannula;

rotating the cutter element and cannula to insert the cannula into position adjacent the target site of the bone;

removing the cutter element from the cannula;

inserting a tissue distraction device into the cannula, the tissue distraction device having a spreader mechanism for moving surrounding tissue away from the target site;

expanding the spreader mechanism to move the tissue away from the target site;

injecting the immobilizing substance through the cannula to the target site; and positioning a plug at a selected site adjacent the target site for retaining the immobilizing substance at the target site of the bone.

* * * * *